United States Patent [19]
Garrison

[11] Patent Number: 5,111,845
[45] Date of Patent: May 12, 1992

[54] PARTITION VALVE FOR FLUID DELIVERY SYSTEM

[75] Inventor: Brevard S. Garrison, Reading, Mass.

[73] Assignee: Millipore Corporation, Mass.

[21] Appl. No.: 633,717

[22] Filed: Dec. 21, 1990

[51] Int. Cl.⁵ .......................................... F16K 11/074
[52] U.S. Cl. .................................. 137/567; 137/597
[58] Field of Search ............... 137/597, 567, 606; 417/395

[56] References Cited

U.S. PATENT DOCUMENTS 2,865,402 12/1958 Miller ........................ 137/597 X
4,037,622 7/1977 Osheroff et al. .................. 137/597

FOREIGN PATENT DOCUMENTS

72961 6/1980 Japan ................................. 137/597

Primary Examiner—Stephen M. Hepperle
Attorney, Agent, or Firm—Andrew T. Karnakis; Paul J. Cook

[57] ABSTRACT

A partition valve for use in a fluid delivery system is provided to deliver precise volumes of plurality of fluids in sequence to a plurality of treatment reservoirs. The partition valve includes a diaphragm having a top surface in contact with a plurality of fluid pressure sources. The bottom surface of the diaphragm contacts a plurality of fluid inlets and outlets. The fluid pressure sources are controlled to effect fluid communication between desired fluid inlets and fluid outlets.

4 Claims, 6 Drawing Sheets

PARTITION VALVE FOR FLUID DELIVERY SYSTEM

BACKGROUND OF THE INVENTION

This invention relates to a partition valve for a fluid delivery system for delivering a plurality of fluids, in sequence to a plurality of treatment reservoirs.

Prior to the present invention, fluid delivery systems have been available which minimize system volume and which minimize intermixing of fluids while delivering a precise amount of a fluid for chemical reaction. These systems are generally utilized for chemical processes involving a large number of sequentially effected chemical reactions such as in protein synthesis, deoxyribonucleic acid (DNA) synthesis or when sequencing proteins.

U.S. Pat. No. 4,008,736 discloses a valve block containing a capillary formed of capillary segments bored at about 30° from a contact surface of the block. The junctions of the capillary segments are effected at the contact surface and within the block. The junctions at the contact surfaces form valving sites to which are engaged apertured sliding blocks which effect fluid communication with the capillary. While the sliding blocks are effective in providing the desired fluid flow, they wear rapidly thereby causing undesirable leaks.

U.S. Pat. No. 4,168,724 discloses a similar device but replaces the slider valves with diaphragm check valves. The fluid is delivered through the check valves from a pressurized fluid storage source. This system requires a vacuum assist to open the valves. This system is undesirable because the type of diaphragm valve used is undesirably susceptible to particulate contamination. In addition, the pressure drop through the valves is difficult to control which causes inaccurate reagent delivery.

U.S. Pat. No. 4,558,845 discloses a fluid delivery system utilizing a valve block assembly comprising a separate block for each valve site. The common conduit to the reaction site is alternately a channel in a block and tubing connecting two adjacent blocks. This arrangement requires a plurality of fittings which are subject to leaking.

U.S. Pat. No. 4,773,446 discloses a valve block assembly which utilizes diaphragm check valves. The check valves serve to control fluid flow from a plurality of pressurized fluid reservoirs, in sequence to a common outlet reservoir. This system requires the use of conduits from the fluid reservoirs and fittings to valve blocks for each conduit. These fittings are subject to leakage.

The fluid delivery system of the prior art depend upon the use of positive pressure to deliver the fluid and upon the control of back pressure to the fluid reservoir in order to precisely control the amount of fluid delivered to a treatment reservoir. These systems require the frequent adjustment of the fluid delivery means as a function of back pressure. All of the systems set forth above depend upon precise control of reservoir pressure and restriction through the valves to control reagent delivery volume. They are very sensitive to variations of the removable reaction column as regards the delivery volume and flow rate. Also these systems deliver fluids against back pressures only up to about 10 psig. It would be desirable to provide a system which eliminates the need of adjustment of the fluid delivery means. It would also be desirable to utilize a means to deliver fluids which is independent of back pressure. Such a system would permit delivery of accurate volumes of reagents which would result in improved system performance and reduced reagent consumption.

SUMMARY OF THE INVENTION

The present invention provides a partition valve for a fluid delivery system for delivering a plurality of fluids in sequence to a treatment reservoir wherein a chemical reaction or a physical treatment step occurs. Channels are formed in a solid plate to which is laminated a sealing layer in order to seal the channels. The surface of the solid plate opposite the surface to which the sealing layer is laminated contains the fluid connections for the means for delivering fluids. The fluids are delivered to a desired point by means of a system comprising the diaphragm check valve, a diaphragm pump and an injector, each in direct fluid communication with the channels in the solid plate. A common outlet channel is connected to sources of a plurality of fluids and the partition valve which directs fluid to a desired destination such as a reaction column. The partition valve has the capacity to direct a plurality of sets of fluids to one of a plurality of desired destinations.

DESCRIPTION OF SPECIFIC EMBODIMENTS

In accordance with this invention, a partition valve is provided for use in a fluid delivery system which directs a plurality of sources of fluids to a desired fluid treatment reservoir. The system is constructed to effect passage of a plurality of fluids in sequence through the system to a plurality of treatment reservoirs. The means for transporting each fluid comprises a check valve, a positive displacement diaphragm pump and an injector which are in direct fluid communication. The check valve is connected to a source of fluid. Each injector in the system is in fluid communication with a common passageway which connects through the partition valve of this invention with a treatment reservoir where chemical reactions are conducted under carefully controlled conditions. Examples of such processes include nucleic acid or protein synthesis and protein sequencing. These processes require sequential chemical reactions which are alternated with washing steps to remove excess unreacted reagent. In some instances, the reagants require a particular atmospheric environment such as an inert environment or an oxidizing environment. In these instances, gases are provided to the fluid reservoir. Therefore, these processes require fluid delivery systems wherein reagent, processing chemicals and gases are processed in a precise manner so that precise volumes of fluid are delivered to the appropriate destination within the system at the proper time and in the proper sequence.

The check valve, diaphragm pump and injector are utilized in connection with each other to deliver a precise volume of fluid from a fluid reservoir to a treatment reservoir. Suitable control means are provided to control the sequence of fluids delivered to the treatment reservoir or reservoirs.

The plate containing the channels for fluid flow is conveniently formed of a ceramic material which can be photoetched to form the channel system in the desired configuration. A surface of the plate contains the channels while the opposing surface of the plate includes the fluid inlets and outlets through which fluid flow is controlled. The surface of the plate including the channels is sealed to a plate member which can be opaque or transparent such as by being formed from glass or plastic. Sealing is effected to seal the channels into the desired flow configuration. The transparent plate member provides the advantage of a direct view to the channel system so aberrations in the system can be observed readily.

The check valve, diaphragm pump and injector system for each fluid as well as the partition valve and remaining components of the system such as the treatment reservoirs are secured to the surface of the plate having the inlets and outlets in a manner so that they communicate with the appropriate fluid inlets and fluid outlets.

The diaphragm pump is a positive displacement pump secured to the plate together with the check valve and the injector. The diaphragm pump can precede the check valve or follow the check valve along the path of fluid flow to the injector. When pressure is increased within the pump, the diaphragm is forced into the plenum and directs to the injector an amount of fluid equal to the volume of the plenum. The fluid, directed to the injector under pressure, forces the diaphragm in the injector to open thereby to effect fluid communication between the injector inlet and the injector outlet and to force fluid from the injector to the treatment reservoir. The pump cavity (plenum) is contoured such that the diaphragm completely purges all liquid from the cavity with each pulse. The shape of the cavity, e.g., spherical, also prevents the diaphragm from being stretched beyond its elastic limit.

The injector includes a housing secured to the plate and a spring-loaded plunger within the housing which is biased toward the plate. An injector diaphragm is positioned between (a) the plunger and (b) the injector inlet and injector outlet on the plate. The end of the plunger is shaped so as to seat the diaphragm against the injector outlet and away from the injector inlet. The area of the diaphragm exposed to the inlet pressure is larger than the area exposed to the outlet pressure. This ratio of exposed areas, for a given pumping pressure provides an increased area at the inlet as compared to the area at the outlet so that the plunger is more easily lifted by pressure applied through the inlet as compared to pressure which may occur at the outlet.

The partition valve of this invention cooperates with channels in a plate which are capable of dividing inlet and outlet streams each into two substreams. The partition valve includes a membrane which contacts the inlets and outlets to the substreams. A plurality of means for changing pressure on a diaphragm surface are provided to effect sealing or effect fluid communication between an inlet of a substream and an adjacent outlet of a substream. The diaphragm and means for changing pressure on the diaphragm are positioned within a housing which maintain the diaphragm and pressure changing means in place with respect to the substream inlets and outlets.

Figure 1:
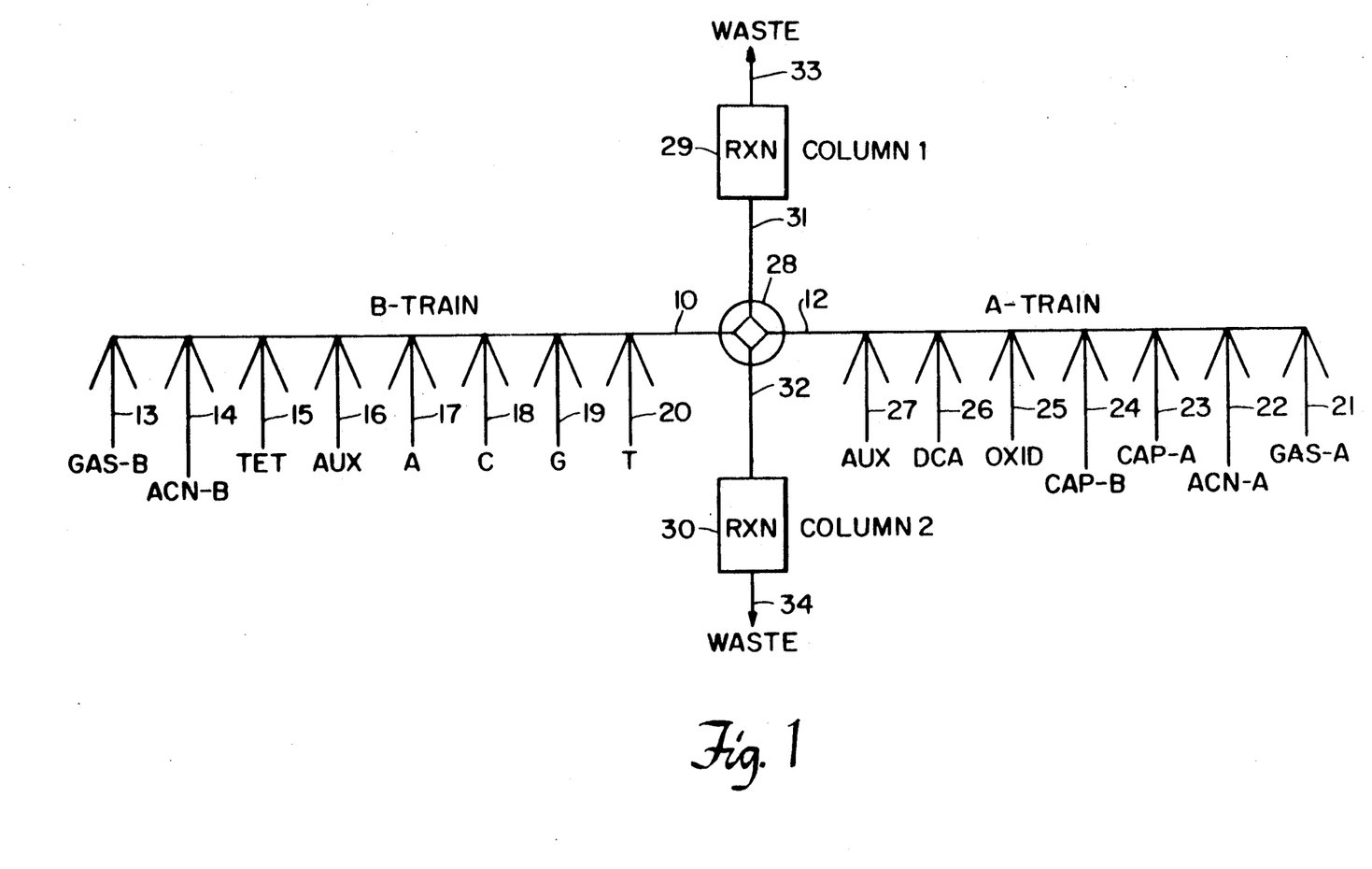
FIG. 1 is a schematic view of a system useful for producing DNA.

The system of the invention will be described with reference to a process for producing polymeric nucleic acids (NA). Referring to FIG. 1 a process for making NA is shown schematically. The process shown utilizes two sets of fluid reagents with one set in fluid communication with common channel 10 and a second set of fluid communication with common channel 12. The first set includes a gas blow-through means for purging the system (Gas B) connected to channel 13, acetonitrile connected to channel 14, tetrazole (TET) connected to channel 15, an auxiliary reservoir (AUX) connected to channel 16, adenosine connected to channel 17, cytidine connected to channel 18, guanosine connected to channel 19 and thymidine connected to channel 20. The second set of fluids include a gas blow-through means for purging the system (GAS-A) connected to channel 21, acetonitrile connected to channel 22, capping solution A (CAP-A) connected to channel 23, capping solution B (CAP-B) connected to channel 24, oxidizer (OXID) connected to channel 25, diochloroacetic acid solution (DCA) connected to channel 26 and auxiliary reservoir (AUX) connected to channel 27. The reagents, adenosine, cytidine, guanosine and thymidine are reagents used to form the DNA as is well known in the art. GAS-A and Gas-B provide the function of purging the system and transporting small volumes of liquid out of the system to a detector. Acetonitrile provides the function of rinsing the system. Acetic anhydride (CAP-A) and N-methylimidazole (CAP-B) provide the function of terminating unreacted sites to prevent further elongation of the failure sequences. OXID provides the function such as iodine in water/pyridine and tetrahydrofuran mixture of oxidizing the elongated chain to stabilize the internucleotide phosphate linkages. DCA provides the function of AUX provides the function of deprotecting the bound residue to permit further condensation reaction. TET provides the function of activating the reactive monomer for the next coupling. Partition valve 28 serves as a switch to direct fluid from either channel 10 or channel 12 to either treatment reservoir 29 comprising a reaction column containing a solid support such as controlled pore glass (CPG) or a membrane through channel 31 or treatment column 30 which is a duplicate of column 29 through channel 32. Channels 33 and 34 direct processed fluid to waste.

Figure 2:
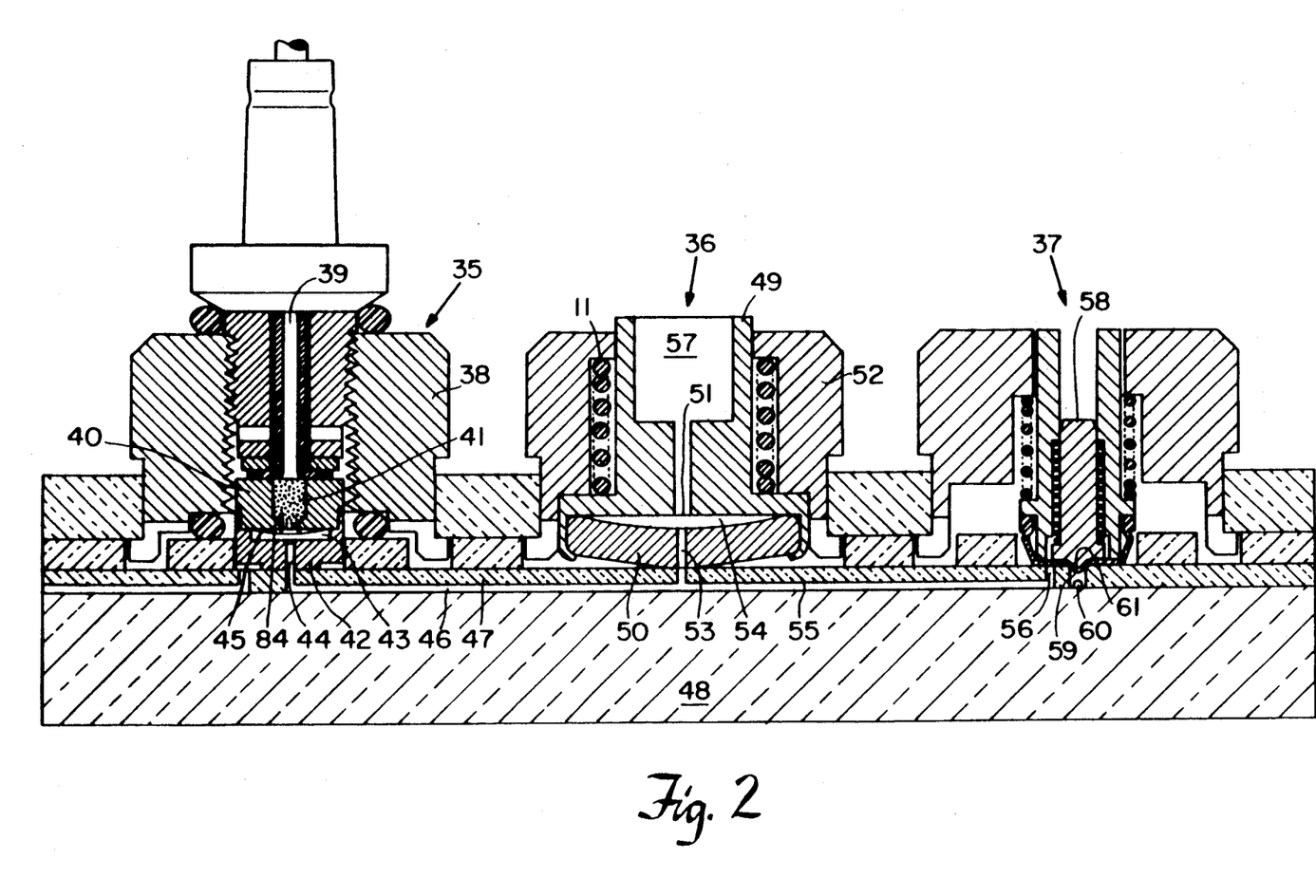
FIG. 2 is a cross-sectional view of a check valve-pump-injector valve unit utilized in this invention.

Referring to FIG. 2, the fluid delivery system of this invention is shown. The fluid delivery system comprises the check valve of this invention 35, a diaphragm pump 36 and an injector 37. The check valve 35 includes housing 38 to which a fitting is attached to accommodate a connection to a fluid reservoir. A top insert 40 includes a cavity 41 housing a filtration means 84. A bottom insert 42 includes a plenum 43 and a check valve outlet 44. A diaphragm 45 is secured between top insert 40 and bottom insert 42. Check valve outlet 44 communicates with channel 46 formed within plate 47. Channel 46 is sealed by a second plate 48 which is preferably transparent. Diaphragm pump 36 comprises a spring 11, a top insert member 49 and a bottom insert member 50 between which is secured diaphragm 51. The inserts 49 and 50 are crimped together and are positioned within housing 52. Channel 46 communicates with pump inlet 53 which, in turn, communicates with pump plenum 54.

Insert 49 contains a cavity 57 to connect to a fluid source which can be opened or closed to alternately apply or remove pressure on the top surface of the diaphragm 51. Pump outlet 53 communicates with channel 55 which communicates with injector inlet 56. Injector 37 includes a plunger 58, an injector diaphragm 59 and injector outlet 60. The end 61 of the plunger 58 is shaped so that the diaphragm 59 seats against outlet 60 and is positioned away from inlet 56. In use, pressure is applied to the fluid within fluid outlet 39 for example about 5 to 10 psig while pressure is reduced within cavity 57. Diaphragm 45 is expanded under pressure, away from inlet 41 and fluid is expelled into outlet 44, channel 46, pump inlet 53 to fill plenum 54 which has a known, fixed volume. When it is desired to expel fluid from cavity 54, high pressure in cavity 57 is effected which causes diaphragm 45 in check valve 35 to close and to cause plunger 58 to be raised and diaphragm 61 to open an injector 37. The pressurized fluid is directed through injector outlet 60. After, the volume of fluid in cavity 54 has been expelled through injector outlet 60, pressure at injector inlet 56 is reduced and plunger 58 returns to the position shown in FIG. 2 wherein access from injector inlet 56 to injector outlet 60 is closed.

Figure 3:
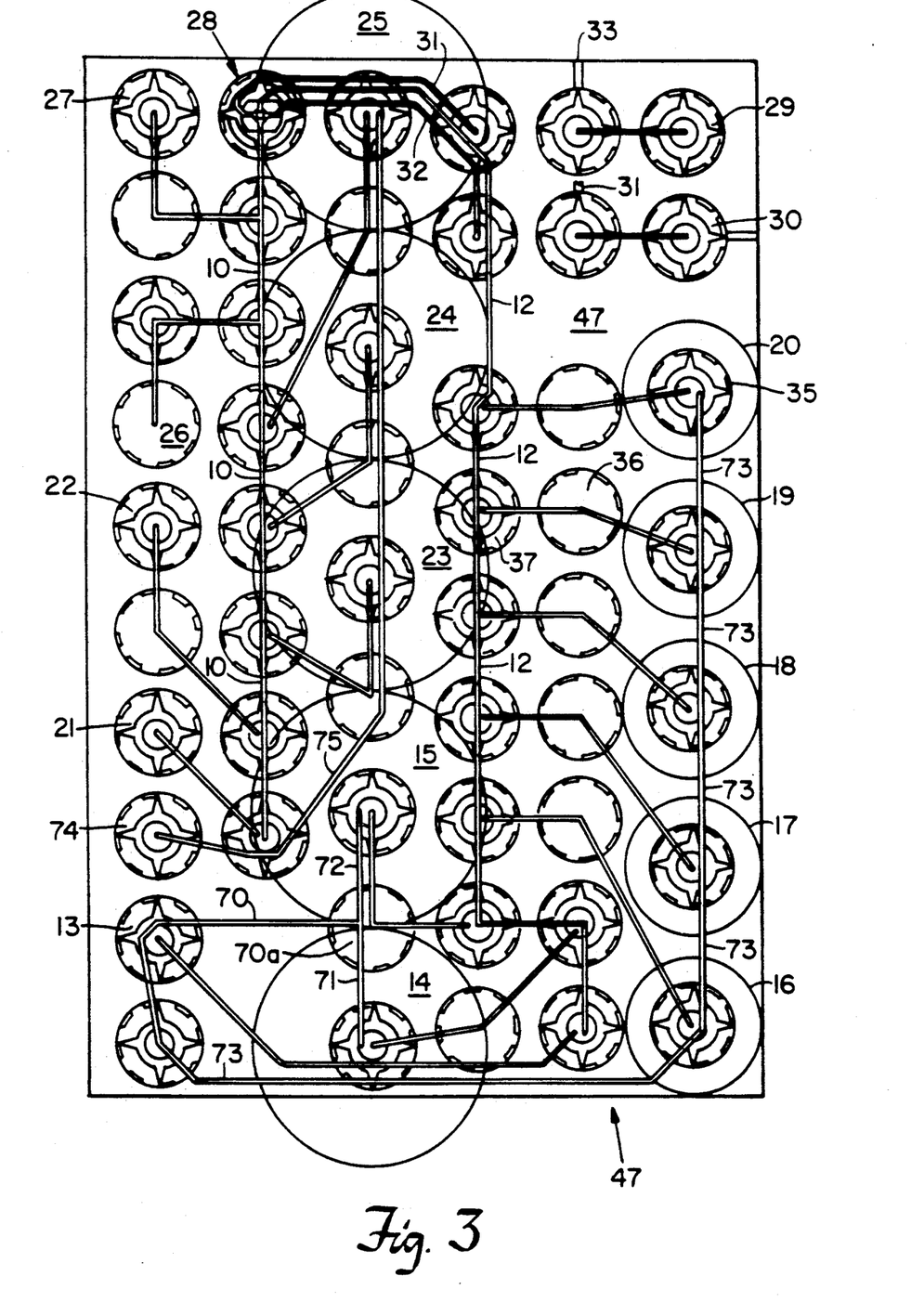
FIG. 3 is a top view of an apparatus utilizing the check valve of this invention useful for implementing the system of FIG. 1.

A function of the system of this invention is described with reference to FIG. 3 and a process for producing DNA. The reactants adenosine, cytidine, guanosine and thymidine are housed in containers 17, 18, 19 and 20 respectively. The system of check valve 35, diaphragm pump 36 and injector 37 functions to direct adenine to channel 12 in plate 47. Duplicate systems of a check valve, a diaphragm pump and injector are utilized for the remaining reactants and are not described in detail herein as to reduce duplication. All of these reactants however, pass from their respective storage containers into channel 12 or channel 10. From channel 12, the reagents pass sequentially to partition valve 28 where they are directed through conduit 31 to reaction column 29 or through conduit 32 to reaction column 30. Subsequent to reaction, the excess reagant passes to waste either through channel 33 or channel 34. Pressurized blanket gas is directed from a container (not shown) attached to and in fluid communication connector 69 and is directed through channel 73 to containers 16, 17, 18, 19 and 20. Sufficient pressure from the blanket gas is applied to open the check valves when the associated diaphragm pumps are not actuated. Similarly, blanket gas is supplied from a container (not shown) through connector 74 through channel 75 to containers 23, 24 and 25. The DCA and ACN-A reservoirs are pressurized by a separate system (not shown). Blow-A and Blow-B provide a means to inject high pressure gas into the system for blowing out the two reagant trains.

Figure 4:
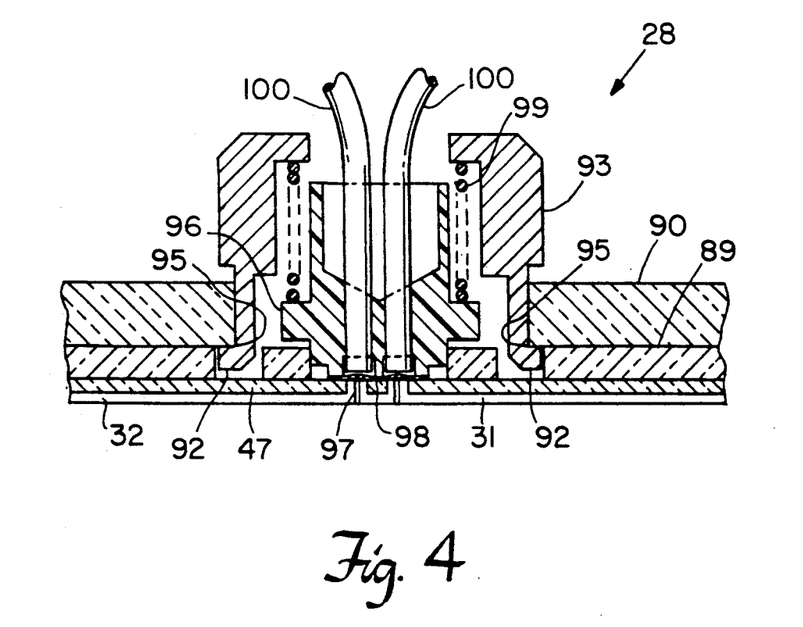
FIG. 4 is a side view, in partial cross section of a partition valve utilized in this invention.
Figure 5:
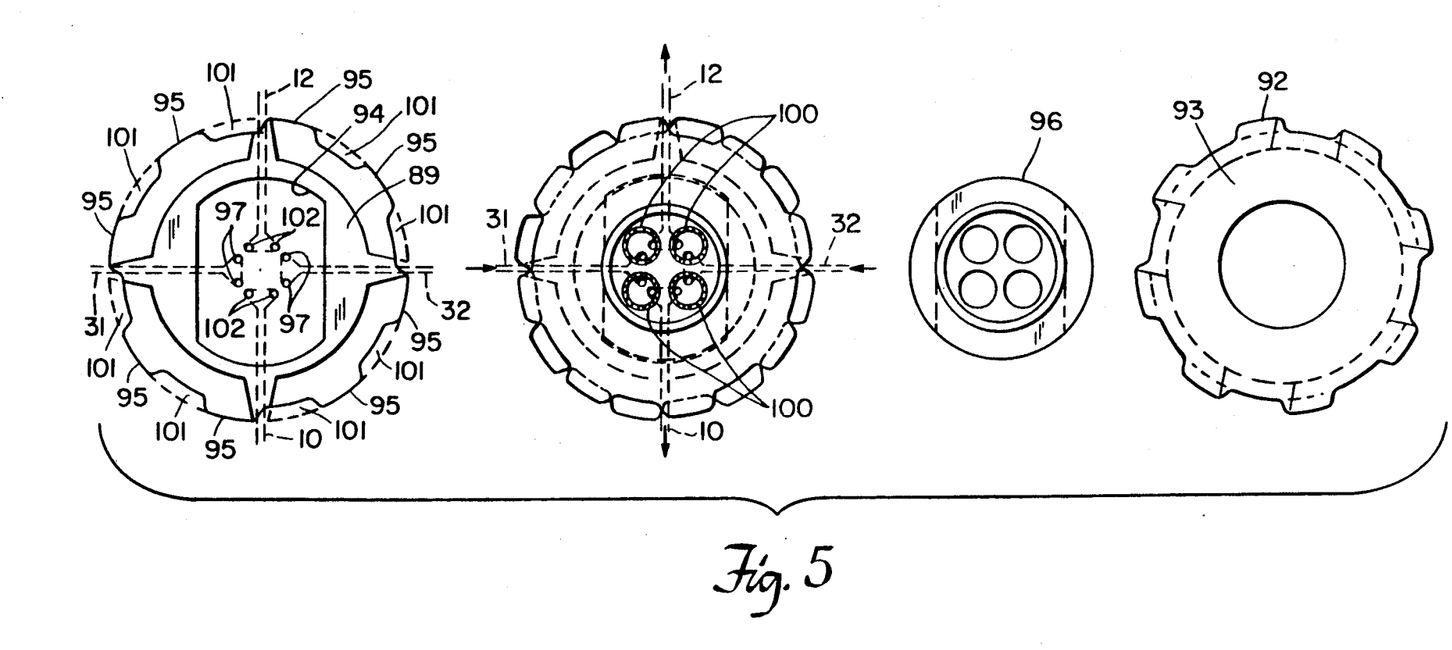
FIG. 5 is an exploded view of the elements forming the partition valve of FIG. 4.
Figure 6:
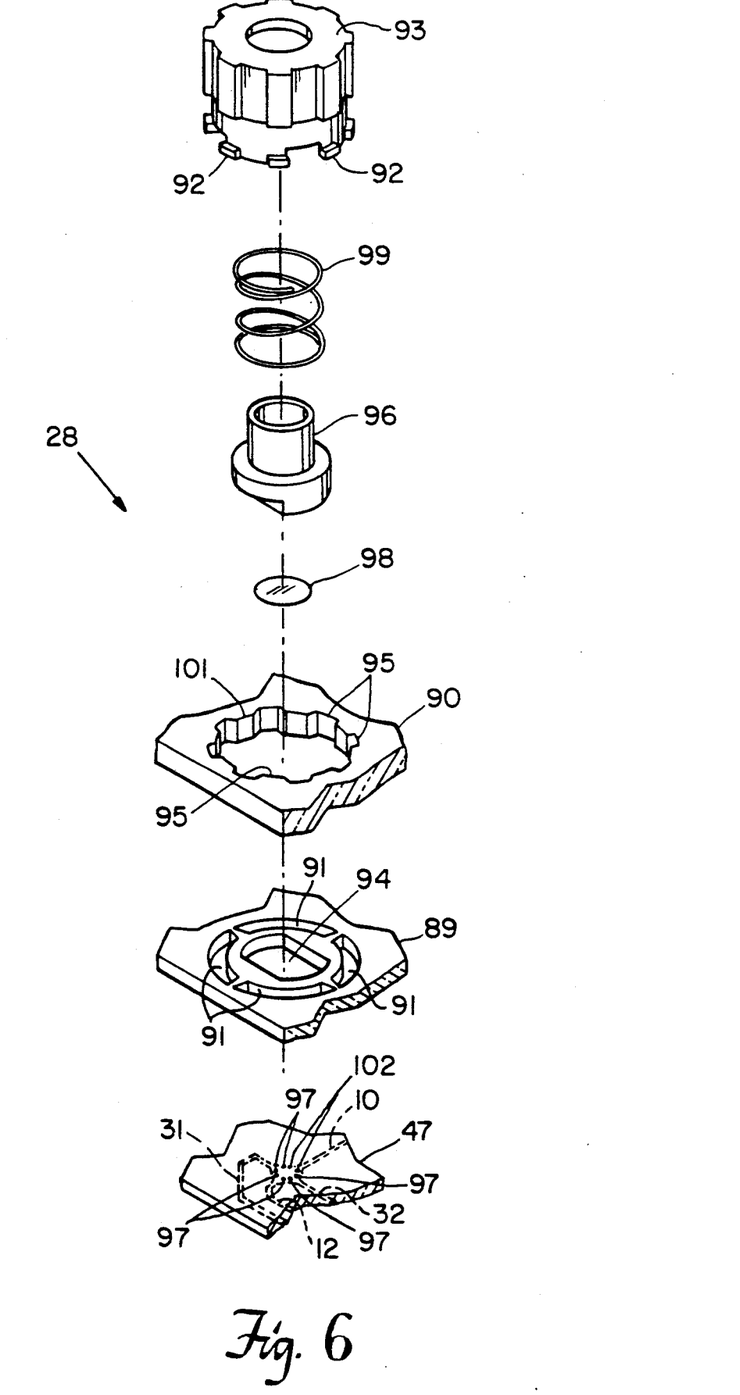
FIG. 6 is an exploded isometric view of the elements forming the partition switch of FIG. 4.

Referring to FIGS. 4, 5 and 6, the partition valve consists of a plurality of elements. As specifically shown in FIG. 6, the ceramic plate includes three layers, 47, 89 and 90. Layer 47 contains channels 10, 12, 31 and 32 of partition valve 28. Layer 89 contains a central opening 94 and peripheral openings 91 into which flanges 92 of housing 93 fit. Layer 90 includes slots 95 into which flanges 92 fit. The housing 93 is passed through the slots 94 and then rotated so that flanges 92 are positioned under extensions 101 to retain housing 93 in place. Prior to positioning the housing 93 in place, the valve body 96 is placed into opening 91 of layer 89 and to position partition valve diaphragm 98 over the substream inlets 102 and substream outlets 97 of layer 47. Layer 89 has opening 91 shaped to maintain the angular position of valve body 96. A spring 99 is provided to retain the valve body 96 in place within housing 93. Four tubes 100 are positioned within valve body 96 over the substream inlets 102 and the substream outlets 97 in layer 47 which communicates with any two of channels 10, 12, 31 and 32 (See FIG. 5). By this arrangement it is possible to control the opening or closing of substream inlets 102 and the substream outlets 97 to selectively open and close them to effect fluid communication between channels 10 or 12 with channels 31 or 32 by exerting or removing pneumatic pressure through selected tubes 100 on selected areas of diaphragm 98. An advantage of this valve is that channel 10 can be processing one reaction vessel while channel 12 is processing a second reaction vessel in parallel rather than sequentially. This partition valve permits processing two reaction vessels as fast as processing one reaction vessel. FIGS. 4–6 are described with reference to a partition valve cooperating with four tubes. However, it is to be understood that the number of tubes is dependent only upon the number of substream inlets and outlets.

I claim:

1. The system for directing a plurality of fluids in sequence from a plurality of fluid reservoirs to a plurality of treatment reservoirs which comprises a fluid transport means for each of said fluid reservoirs comprising a check valve, a diaphragm pump and an injector in fluid communication with each of said reservoirs;

said check valve having a check valve inlet, a check valve outlet, a diaphragm positioned between said check valve inlet and said check valve outlet, and means for positioning said diaphragm between a position for preventing fluid communication between said check valve inlet and said check valve outlet and a position for permitting fluid communication between said check valve inlet and said check valve outlet;

said diaphragm pump including a plenum and a pump diaphragm and means for moving said pump diaphragm between a position for filling said plenum with fluid and for emptying said plenum of fluid;

said injector including an injector diaphragm positioned between an injector inlet and an injector outlet, means for moving said injector diaphragm between a position for providing fluid communication between said injector inlet and said injector outlet and a second position for preventing fluid communication between said injector inlet and said injector outlet;

plate means including passageways for providing fluid communication between said check valve, said diaphragm pump and said injector at least one common channel in fluid communication with a plurality of said injectors and a partition valve for directing fluid from one of a plurality of said common channels to one of a plurality of said treatment reservoirs, said partition valve comprising a plurality of inlet channels and a plurality of outlet channels, each of said inlet channels being subdivided into a plurality of substream inlets, each of said outlet channels being subdivided into a plurality of substream outlets, a partition diaphragm having a first surface in contact with said substream inlets and said substream outlets, means for selectively pressurizing a second surface of said partition diaphragm to effect either fluid communication between a substream inlet and an adjacent substream outlet or to prevent fluid communication between a substream inlet and an adjacent substream outlet, and means for retaining said partition diaphragm and said means for pressurizing in a desired position relative to said substream inlets and said substreams outlets.

2. The system of claim 1 wherein said means for selectively pressurizing comprises a plurality of conduits and a source of pressurized fluid in fluid communication with said conduits.

3. The system for directing a plurality of fluids in sequence to two treatment reservoirs which comprises a fluid transport means for each of said fluid reservoirs comprising a check valve, a diaphragm pump and an injector in fluid communication with each of said reservoirs;

said check valve having a check valve inlet, a check valve outlet, a diaphragm positioned between said check valve inlet and said check valve outlet, and means for positioning said diaphragm between a position for preventing fluid communication between said check valve inlet and said check valve outlet and a position for permitting fluid communication between said check valve inlet and said check valve outlet;

said diaphragm pump including a plenum and a pump diaphragm and means for moving said pump diaphragm between a position for filling said plenum with fluid and for emptying said plenum of fluid;

said injector including an injector diaphragm positioned between an injector inlet and an injector outlet, means for moving said injector diaphragm between a first position for providing fluid communication between said injector inlet and said injector outlet and a second position preventing fluid communication between said injector inlet and said injector outlet;

plate means including passageways for providing fluid communication between said check valve, said diaphragm pump and said injector;

a first common channel for a first set of fluids, a second common channel for a second set of fluids, and a partition valve for directing fluid from said first common channel and said second common channel to a first treatment reservoir and to said second treatment reservoir.

said partition valve comprising a plurality of inlet channels and a plurality of outlet channels, each of said inlet channels being subdivided into a plurality of substream inlets, each of said outlet channels being subdivided into a plurality of substream outlets, a partition diaphragm having a first surface in contact with said substream inlets and said substream outlets, means for selectively pressurizing a second surface of said partition diaphragm to effect either fluid communication between a substream inlet and an adjacent substream outlet or to prevent fluid communication between a substream inlet and an adjacent substream outlet, and means for retaining said partition diaphragm and said means for pressurizing in a desired position relative to said substream inlets and said substream outlets.

4. The system of claim 3 wherein said means for selectively pressurizing comprises a plurality of conduits and a source of pressurized fluid in fluid communication with said conduits.

* * * * *